United States Patent [19]
Zare et al.

[11] Patent Number: 5,903,358
[45] Date of Patent: May 11, 1999

[54] SPECTROSCOPY USING ACTIVE DIODE LASER STABILIZATION BY OPTICAL FEEDBACK

[75] Inventors: Richard N. Zare, Stanford, Calif.; Juergen Martin, Harxheim, Germany; Barbara A. Paldus, Stanford, Calif.

[73] Assignee: The Board of Trustees of the Leland Stanford Junior University, Stanford, Calif.

[21] Appl. No.: 08/949,241

[22] Filed: Oct. 10, 1997

Related U.S. Application Data

[63] Continuation-in-part of application No. 08/879,975, Jun. 20, 1997.
[51] Int. Cl.[6] .................................................. G01N 21/17
[52] U.S. Cl. ......................... 356/437; 356/440; 250/343
[58] Field of Search .................................. 356/432, 437, 356/439, 440; 250/343

[56] References Cited

U.S. PATENT DOCUMENTS

| | | | |
|---|---|---|---|
| 5,528,040 | 6/1996 | Lehmann | 250/343 |
| 5,757,831 | 5/1998 | Kmetec et al. | 372/26 |

OTHER PUBLICATIONS

Romanini, R. et al,; *Diode Laser Cavity Ring Down Spectroscopy*; Chemical Physics Letters 270; May 30, 1997; pp. 538–545.

Romanini, R. et al.; *CE Cavity Ring Down Spectroscopy*; Chemical Physics Letters 364; Jan. 10, 1997; pp. 316–322.

Martin, J. et al.; *Visible–Wavelength Diode Laser with Weak frequency–Shifted Optical Feedback*; Optics Communications 112; Nov. 1, 1994; pp. 109–121.

*Primary Examiner*—Richard A. Rosenberger
*Attorney, Agent, or Firm*—Lumen Intellectual Property Services

[57] ABSTRACT

A cavity ring down spectroscopy (CRDS) system uses a free-running continuous wave (c.w.) diode laser stabilized by frequency-shifted optical feedback in the presence of strong reflections from a high-finesse Fabry-Perot resonator. The frequency-shifted feedback stabilization eliminates the need for tightly controlling the relative positions of the laser and resonator. Non-frequency-shifted feedback is used for linewidth broadening. An acousto-optic modulator placed between the diode laser output and the resonator input frequency-shifts light reflected by the resonator input, causing the laser to cycle in phase with a period equal to the inverse of the frequency-shift. The laser diode linewidth can be stabilized from several MHz for high resolution spectroscopy of species at low pressures, to several hundred MHz for lower resolution spectroscopy of species at atmospheric pressures.

23 Claims, 5 Drawing Sheets

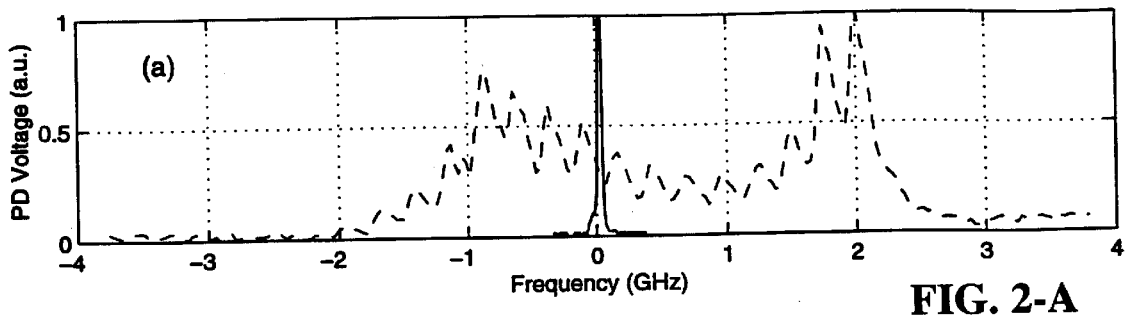
FIG. 2-A
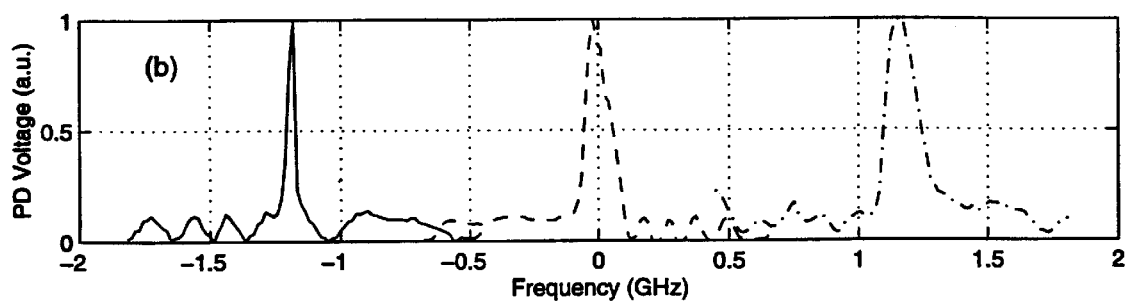
FIG. 2-B
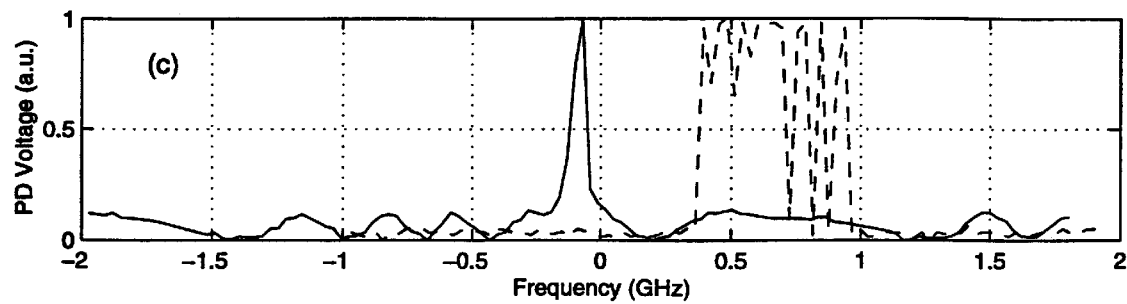
FIG. 2-C

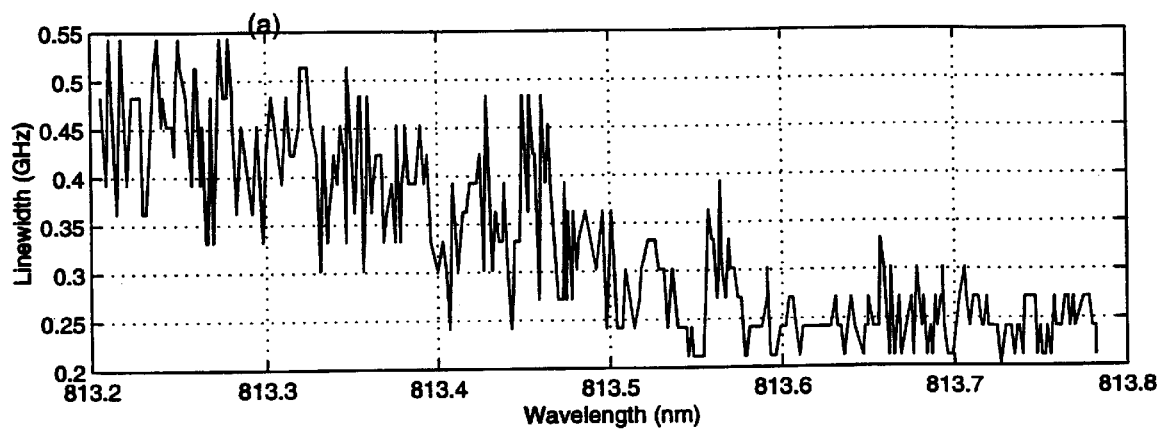
FIG. 3-A
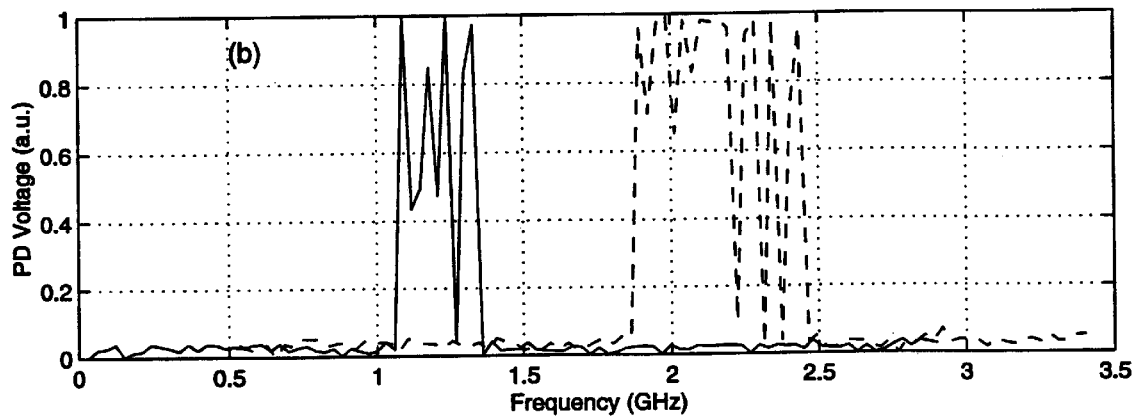
FIG. 3-B

FIG. 4-A
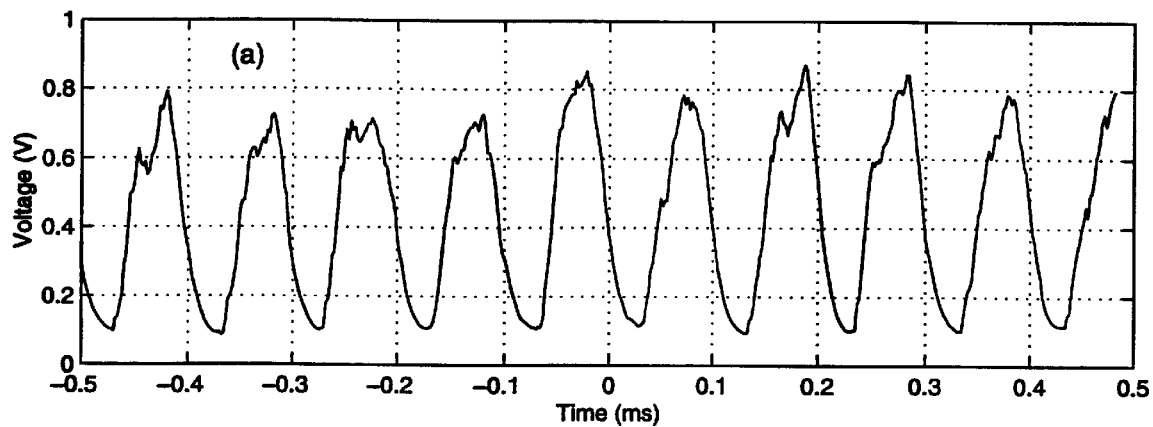
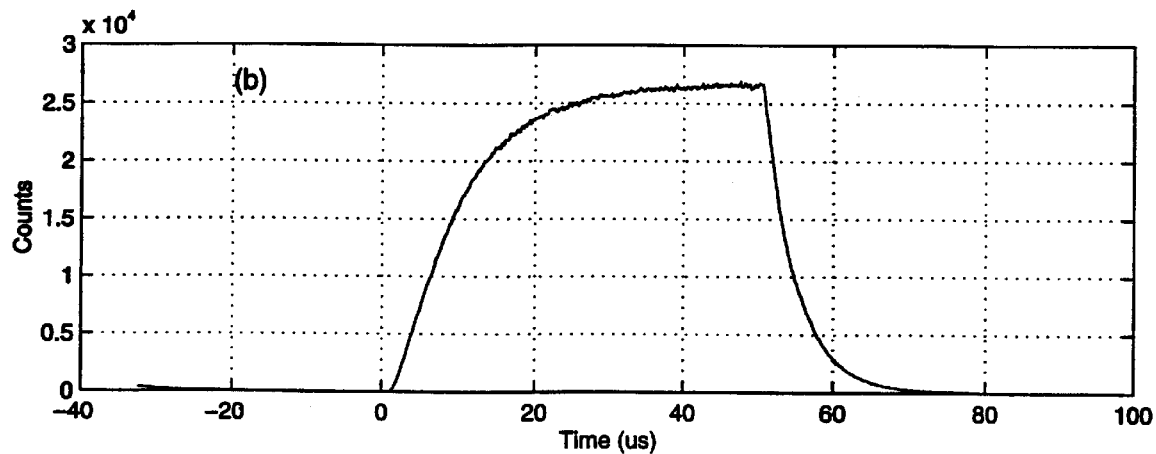
FIG. 4-B

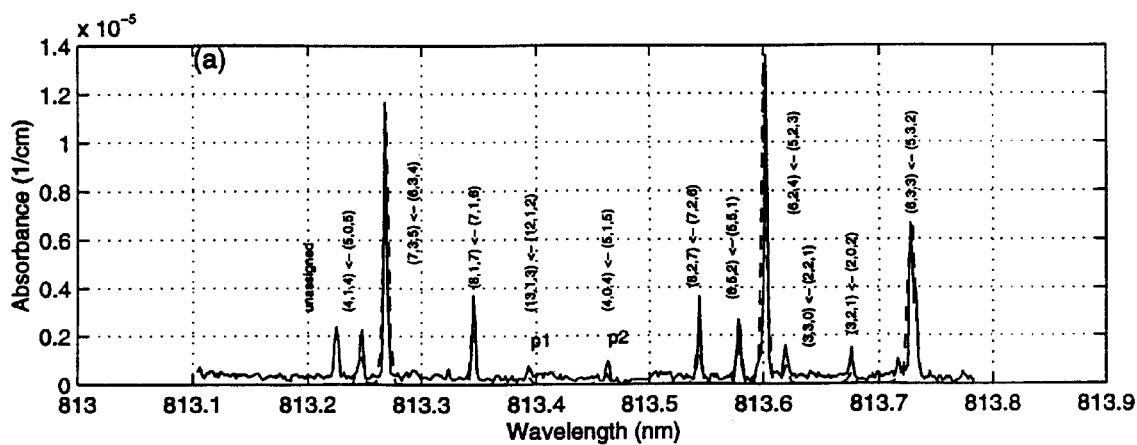
FIG. 5-A
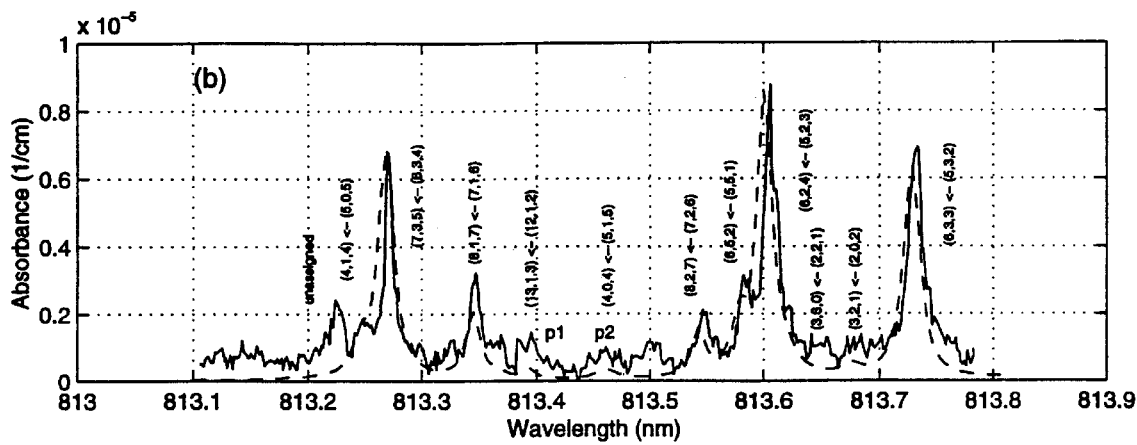
FIG. 5-B

SPECTROSCOPY USING ACTIVE DIODE LASER STABILIZATION BY OPTICAL FEEDBACK

RELATED APPLICATION DATA

This application is a continuation-in-part of U.S. patent application Ser. No. 08/879,975, filed Jun. 20, 1997, which is assigned to the assignee of the present invention and is herein incorporated by reference.

U.S. GOVERNMENT RIGHTS

This invention was made with U.S. Government support under DOE grant No. DE-FG03-92ER14304 and ARPA-ONR contract No. N00014-92-J-1903. The U.S. Government has certain rights in this invention.

FIELD OF THE INVENTION

This invention relates to spectroscopy using diode lasers, and in particular to optical feedback stabilization for diode lasers in cavity ring-down spectroscopy.

BACKGROUND OF THE INVENTION

Traditional spectroscopic methods are limited in sensitivity to approximately one part per ten thousand ($1:10^4$) to one part per hundred thousand ($1:10^5$). The sensitivity limitation arises from instabilities in light source intensity that are translated into noise in the absorption signal. For general information on traditional spectroscopy methods see for example Dereniak and Crowe, *Optical Radiation Detectors*, John Wiley & Sons, New York, 1984, and Demtröder, *Laser Spectroscoptpy*, Springer, Berlin, 1996.

Cavity Ring-Down Spectroscopy (CRDS), a technique first described by O'Keefe and Deacon in an article in *Rev. Sci. Instrum.* 59(12):2544–2551 (1988), allows making absorption measurements with sensitivities on the order of one part per ten million ($1:10^7$) to one part per billion ($1:10^9$) or higher. For general information on CRDS see U.S. Pat. No. 5,528,040 by Lehmann, herein incorporated by reference, as well as the articles by Romanini and Lehmann in *J. Chem. Phys.* 102(2):633–642 (1995), Meijer et al. in *Chem. Phys. Lett.* 217(1–2):112–116 (1994), Zalicki et al. in *App. Phys. Lett.* 67(1):144–146 (1995), Jongma et al. in *Rev. Sci. Instrum.* 66(4):2821–2828 (1995), and Zalicki and Zare in *J. Chem. Phys.* 102(7):2708–2717 (1995).

In a conventional CRDS system, the sample (absorbing material) is placed in a high-finesse stable optical resonator consisting of two spherical mirrors facing each other along a common optical axis. Light incident on one mirror circulates back and forth multiple times in the resonator, setting up standing waves having periodic spatial variations. Light exiting through the other mirror measures the intracavity light intensity.

The radiant energy stored in the resonator decreases in time (rings-down). For an empty cavity, the stored energy follows an exponential decay characterized by a ring-down rate that depends only on the reflectivity of the mirrors, the separation between the mirrors, and the speed of light in the cavity. If a sample is placed in the resonator, the ring-down is accelerated; under suitable conditions, the intracavity energy decays almost perfectly exponentially. An absorption spectrum for the sample is obtained by plotting the reciprocal of the ring-down rate versus the wavelength of the incident light. CRDS has been applied to numerous systems in the visible, ultraviolet, and infrared. For information on the use of CRDS for spectroscopy in the visible, see the articles by Engeln and Meijer in *Rev. Sci. Instrum.* 67(8):2708–2713 (1996), Martin et al. in *Chem. Phys. Lett.* 258(1–2):63–70 (1996), Paul et al. in *J. Chem. Phys.* 104(8):2782–2788 (1996), Scherer et al. in *J. Chem. Phys.* 103(21):9187–9192 (1995), Scherer et al. in *J. Chem. Phys.* 102(13):5190–5199 (1995), Scherer et al. in *Chem. Phys. Lett.* 242(4–5):395–400 (1995). Heustis et al. in *Canadian J. Phys.* 72(11–12):1109–1121 (1994), and O'Keefe et al. in *Chem. Phys. Lett.* 172(3–4):214–218 (1990). Information on CRDS applications in the ultraviolet can be found in the above-referenced articles by Romanini and Lehmann, and Zalicki et al., as well as the articles by Zhu et al. in *Chem. Phys. Lett.* 257(5–6):487–491 (1996), Romanini and Lehmann in *J. Chem. Phys.* 105(1):81–88 (1996), Romanini and Lehmann in *J. Chem. Phys.* 105(1):68–80 (1996), Wahl et al. in *Diamond and Related Materials* 5(3–5):373–377 (1996) Boogaarts and Meijer in *J. Chem. Phys.* 103(13):5269–5274 (1995), Zalicki et al. in *Chem. Phys. Lett.* 234(4–6), 269–274 (1995), Jongma et al. in *J. Molecular Spectroscopy* 165(2):303–314 (1994), and Romanini and Lehmann in *J. Chem. Phys.* 99(9):6283–6301 (1993). For information on the use of CRDS for infrared spectroscopy see the above-referenced article by Martin et al. (1996), as well as the article by Scherer et al. in *Chem. Phys. Lett.* 245(2–3):273–280 (1995).

In comparison to conventional spectroscopy techniques, CRDS is advantageous because of the increased pathlength due to multiple reflections. CRDS is also advantageous because of its relative insensitivity to variations in the amplitude of light generated by the light source. In a CRDS system, fluctuations in the intensity of the light source do not typically limit sensitivity.

Much of current ring-down spectroscopy still relies on fairly costly laser sources. As solid state lasers (e.g. Ti:Sapphire lasers, Nd:Yag-pumped OPOs, and ECDLs) have gained in reliability, tuning range, and output power, they have started to replace the more traditional tunable dye lasers, although they are no less expensive. Simultaneously, semiconductor diode lasers (DL) have also been improving in power, wavelength coverage, and reliability. The rapid growth of the communications industry in recent years has resulted in the availability of tunable near-infrared DLs at a rapidly diminishing cost. In fact, owing to their compactness, low cost, durability, high wallplug efficiency, and compatibility with both fiber and silicon technologies, infrared diode lasers are a promising light source for practical CRDS systems.

Early attempts have demonstrated difficulties in using DL sources in conventional CRDS systems. As long as the linewidth of the resonator is much narrower than the laser linewidth (as in most systems), only a small fraction of the light incident on the resonator enters the resonator; most of the light is reflected back toward the laser. Even under optical isolation, the optical feedback typically results in excess noise in the laser's frequency stability, mode oscillation stability, and power output. The excess laser noise leads to unstable laser-resonator coupling, increased baseline noise, and reduced absolute sensitivity for absorption measurements. Back-reflections also lead to an increase in laser linewidth, which limits spectral resolution. At high feedback levels typical in most practical setups, a wide variety of effects ranging from linewidth broadening to complete 'coherence collapse' (linewidth >10 GHz) are often observed (see FIG. 2).

The DL instabilities are due to 'external cavities' formed between reflective optics and the facets of the DL. Since diode lasers typically have large gain bandwidths (around 40 nm), virtually any external cavity can become optically coupled to the diode laser and influence its behavior. Because the output facet of the DL has a low reflectivity or is antireflection (AR)-coated to increase output power, the dominant laser cavity (the cavity determining laser behavior) in a conventional system is formed between the back facet of the DL and the resonator input, rather than between the DL facets. The dominant external cavity affects both the gain and phase relations of the DL, as explained for example by Petermann in *Laser Diode Modulation and Noise*, Kluwer Academic Publishers, Dordrecht, 1988, p. 250–285, Agrawal and Dutta in *Semiconductor Lasers*, Van Nostrand Reinhold, New York, 1993, p. 258–309, and Coldren and Corzine in *Diode Lasers and Photonic Integrated Circuits*, John Wiley and Sons, New York, 1995, p. 221–257. Whenever back reflection is allowed, the lasing characteristics of the DL (frequency, number of excited modes, output power, etc.) typically become highly dependent on uncontrollable experimental parameters, most notably external cavity length(s).

A CRDS system making use of a diode laser as a light source is described in the article by Romanini et al. in *Chem. Phys. Lett.* 270:538–545 (1997), herein incorporated by reference. Romanini et al. noted that without stringent optical isolation (in excess of 70 dB), any backreflections from the ring-down resonator caused serious mode-hopping and transverse mode excitation in their laser. Romanini et al. also noted that a single-pass high-dB Faraday isolator was "absolutely needed," and that an acousto-optic modulator alone was not adequate for optical isolation as in the case of dye lasers.

The above-incorporated U.S. Pat. No. 5,528,040 (Lehmann) suggests the use of a diode laser in a continuous-wave (c.w.) CRDS system. The system described by Lehman did not ensure adequate optical isolation and was thus subject to significant diode laser instability problems. Even the substantial isolation level (60 dB) used by Lehmann was not sufficient for adequately reducing laser instability caused by back reflections into the diode laser.

A preliminary report on the use of c.w. diode lasers for CRDS can be found in the abstract by Romanini et al. in *Proceedings of the 50th International Symposium on Molecular Spectroscopy*, ed. T. A. Miller (Department of Chemistry, Ohio State University. Columbus, Ohio), 1995, p. 284. The potential use of c.w. diode lasers for CRDS is also discussed in the article by Romanini et al. in *Chem. Phys. Lett.* 264:316–322 (1997), herein incorporated by reference.

A solution to the coupling/feedback problem is described in the above-incorporated co-pending U.S. patent application Ser. No. 08/879,975. The feedback from the resonant cavity is completely eliminated through the use of a ring resonator geometry, in which reflections from the resonator input are not directed back towards the laser.

The present invention provides a novel solution to the problem of optical feedback from a resonant spectroscopy cavity to a diode laser. Optical feedback from a resonant cavity to a diode laser is of concern for various non-CRDS spectroscopy applications. For information on non-CRDS spectroscopy systems see for example U.S. Pat. Nos. 5,173,749 and 5,432,610. A method of stabilizing diode lasers in the presence of optical feedback from a resonant cavity would find use in many non-CRDS spectroscopy applications.

OBJECTS AND ADVANTAGES OF THE INVENTION

In light of the above, it is a primary object of the present invention to provide a robust and stable spectroscopy system using a diode laser as a light source. It is another object to provide a stable CRDS system comprising a diode laser. It is another object to provide for active diode laser stabilization in a spectroscopy system, using frequency-shifted optical feedback of a suitable intensity (feedback level). It is yet another object to provide for diode laser stabilization such that the diode laser is relatively insensitive to mechanical instabilities in external cavities enclosing the diode laser. It is still another object to provide for diode laser stabilization using an acousto-optic modulator and feedback control elements situated between the diode laser output and the input of the sample-holding resonant cavity. Another object is to allow controlling the diode laser linewidth by choosing appropriate levels of frequency-shifted and non-frequency-shifted feedback.

SUMMARY OF THE INVENTION

A system of the present invention comprises a diode laser having a laser output, a resonant cavity having a cavity input and a cavity output, a laser stabilization means in optical communication with the laser output, and a detection means in optical communication with the cavity output. The laser is preferably an infrared continuous wave (c.w.) tunable laser. The diode laser is preferably not an external-cavity laser, such that its output is defined by the output facet of the diode itself; such output facets typically have reflectivities of less than 20%, in many cases less than 5%. The resonant cavity defines an intracavity light path passing through a sample. The resonant cavity is situated relative to the diode laser and the detection means such that light extending from the laser output is incident on the cavity input, follows the intracavity light path, exits through the cavity output, and is incident on the detection means. The detection means detects light extending from the cavity output, thus measuring the interaction of the sample with intracavity light at each wavelength of a spectrum of interest. Stable operation of the diode laser is ensured by the laser stabilization means, which provides frequency-shifted feedback light incident on the laser. The frequency-shifted feedback light is of a level suitable for actively stabilizing the laser. The frequency-shifted feedback level is generally between −35 dB and −65 dB, preferably between −45 dB and −55 dB.

The laser stabilization means preferably comprises an acoustooptic modulator (AOM) for producing the frequency-shifted feedback light by frequency-shifting light generated by the laser. The first order (frequency-shifted) diffracted light generated by the AOM is incident on the cavity input. The AOM also acts as a switching means for switching on and off the first-order light incident on the cavity input; when the AOM is off, no first order beam is generated. A driving means drives the AOM and controls the efficiency of its diffraction, thus partially controlling the intensity of the frequency-shifted feedback light incident on the laser output. The intensity of the frequency-shifted feedback light is primarily controlled by an optical isolator situated between the AOM and the laser output. The optical isolator reduces the intensity of the frequency-shifted feedback light to the desired suitable level, and also isolates the laser from direct, non-frequency-shifted reflections from the AOM.

A linewidth broadening means is in optical communication with the laser output, and provides non-frequency-shifted feedback light incident on the laser output. The non-frequency-shifted feedback light increases the linewidth of the diode laser. The intensity of the non-frequency-shifted feedback light is preferably within an order of magnitude of that of the frequency-shifted feedback light. Varying the relative intensity of the non-frequency-shifted feedback light allows adjusting the linewidth of the diode laser to predetermined values. The linewidth broadening means preferably comprises reflective optics for reflecting the zeroth order light generated by the AOM back into the laser.

A data analysis means is in electrical communication with the detection means. The data analysis means receives from the detection means signals characterizing the intensity of light extending from the laser output. The signals implicitly characterize the interaction between the sample and intracavity light. The time-dependence of the intracavity light intensity of a given wavelength is determined by the absorption of the sample at that wavelength. The data analysis means uses the received signals to determine values of parameters of interest characterizing the time-dependence of the intracavity light intensity. Preferred parameters of interest include exponential rates characterizing the time dependence, and in particular ring-down rates. The data analysis means generates an absorption spectrum of the sample from ring-down data at various wavelengths.

DESCRIPTION OF THE FIGURES

FIG. 2-A shows linewidths for a prior-art unstabilized diode laser, and for a diode laser stabilized with optical feedback according to the present invention.

FIG. 2-B shows linewidths as a function of cavity length for a diode laser stabilized according to the present invention.

FIG. 2-C shows linewidths for a laser under frequency-shifted feedback only, and under frequency-shifted and non-frequency-shifted feedback, according to the present invention.

FIG. 3-A illustrates the dependence of linewidth with wavelength for a feedback-stabilized diode laser of the present invention.

FIG. 3-B shows the spectral output at two wavelengths of a feedback-stabilized diode laser of the present invention.

FIG. 4-A shows ring-down waveforms as recorded using an oscilloscope, wherein each data point contains the average of 300 shots, according to the present invention.

FIG. 4-B shows a ring-down waveform as recorded using a multichannel scalar, wherein each data point contains the average of 5000 shots, according to the present invention.

FIG. 5-A shows a spectrum of water vapor in room air recorded using a device of the present invention (solid line), and a prior-art water spectrum (dashed line).

FIG. 5-B shows a spectrum of water vapor in at 5 Torr recorded using a device of the present invention (solid line), and a prior-art water spectrum (dashed line).

DETAILED DESCRIPTION

Figure 1:
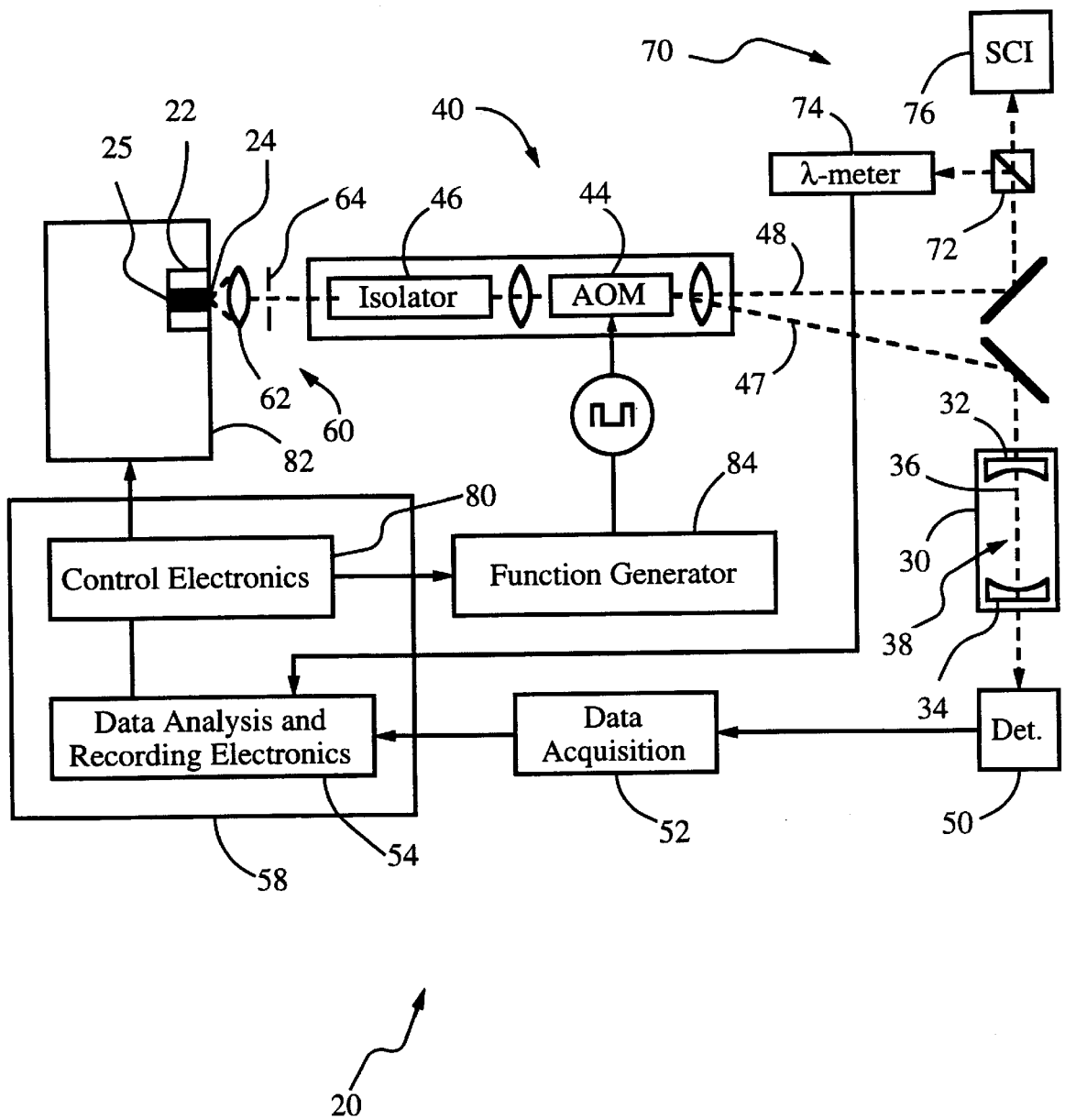
FIG. 1 is a schematic diagram of a system of the present invention.

FIG. 1 is a schematic diagram of a system 20 of the present invention. In FIG. 1, light beams are illustrated by dashed lines, while electrical connections are illustrated by solid lines. For clarity of presentation, various standard elements such as lenses and mirrors used for focusing and directing beams are not described; such elements are well known in the art.

System 20 comprises a tunable diode laser 22 having a laser output facet 24 and a high reflectivity back facet 25. Diode laser 22 emits light within a wavelength region of interest, commonly a wavelength region in which a sample has absorption features. Suitable wavelength regions of interest include the infrared, the visible, and the ultraviolet. Diode laser 22 is preferably capable of emitting infrared light. Diode laser 22 is preferably a continuous wave (c.w.) laser; c.w. lasers are generally capable of producing narrower linewidths than pulsed lasers. Back mirror 25 has a high reflectivity, preferably >90%. Laser output 24 is a diode output facet (mirror) having a low reflectivity—less than 20%, and preferably less than 5%.

Laser 22 is controlled by a conventional laser controller 82 which includes current and temperature stabilization components. Laser controller 82 is used to tune diode laser 22 thermally and electrically; small tuning steps are performed by altering the current through diode laser 22, while larger tuning increments are achieved through temperature excursions. Control electronics 80 are electrically connected to a controller 82 and to a function generator 84. Focusing and collimation optics 60 comprise a laser collimation lens 62 for focusing the divergent light beam emerging through laser output 24, and a pinhole 64 for isolating laser 22 from back-reflections not along the optical axis of system 20.

A cavity input 32 of a ring-down resonant cavity 30 is in optical communication with laser output 24, such that light extending from laser output 24 is incident on cavity input 32. Optional beam shaping optics such as a beam expander and mode-matching lenses (not shown) may be provided in front of cavity input 32. Cavity 30 is a high-finesse optical resonator (Fabry-Perot cavity). Cavity 30 further comprises a cavity output 34, and defines an intracavity light path 36 between cavity input 32 and cavity output 34. Cavity input 32 and cavity output 34 are high-reflectivity (>95%, but less than 100%) mirrors. Cavity 30 has a physical length of less than one meter, and an effective intracavity pathlength two to five orders of magnitude higher than its physical length. Cavity 30 preferably has a linear geometry, in which light is incident onto cavity input 32 orthogonally such that light reflected from cavity input 32 is colinear with light incident on cavity 30. The length of cavity 30 is either constant or changeable by linear motion of either input 32 or output 34, as desired for maximizing the coupling of light into cavity 30. A sample 38 is situated within light path 36. Sample 36 is preferably a gas situated within the entirety of intracavity light path 36, but in general may be solid or liquid, and may be situated anywhere within light path 36.

Since laser output 24 has a low reflectivity, the behavior of diode laser 22 is to a large extent determined by the external cavity defined by cavity input 32 and back mirror 25. Reflections from cavity input 32 substantially affect the operation of diode laser 22, even in the presence of moderate to high levels of isolation.

Optical diagnostic elements 70 are in optical communication with laser output 24, for analyzing a diagnostic beam 48 and implicitly light entering cavity 30. A beam splitter 72 preferably sends parts of diagnostic beam 48 to a wavelength-meter 74 and/or to a scanning-confocal (SCI) interferometer 76. Wavelength meter 74 is connected and sends data to data analysis electronics 54. Other suitable diagnostic elements may include a CCD camera for analyzing the transverse spatial distribution of diagnostic beam 48, for example. Generally, diagnostics could also be performed by splitting off part of beam 47.

A detector 50 is in optical communication with cavity output 34, and detects light extending from cavity output 34, measuring the interaction of sample 38 with intracavity light of a spectrum of frequencies. Detector 50 is preferably a photomultiplier tube; alternatively, detector 50 can include an avalanche photodiode or a photodiode connected to an amplifier. A data acquisition device 52 is in electrical communication with detector 50, for generating a waveform indicative of the time dependence of the signals from detector 50. Device 52 can be any A/D converter or photon counter such as a scalar, an oscilloscope, a boxcar integrator, or a custom made A/D board. Data analysis and recording electronics 54 are in electrical communication with device 52 (and implicitly with detector 50), and determine values of various parameters of interest from signals characterizing the interaction of intracavity light with sample 38. Preferably, the parameters of interest include parameters measuring the time-dependence of the intracavity light intensity, and in particular ring-down rates for a spectrum of light wavelengths. Absorption spectra may be used for evaluating known compositions or for trace species detection.

In an embodiment suited for research applications, the functions of control electronics 80 and data analysis electronics 54 are performed by a personal computer 58. In embodiments suited for industrial applications, all electronic and optical components are preferably integrated in a compact system.

As discussed above, diode lasers are extremely sensitive to optical feedback, even at levels below −80 dB. In weak feedback regimes, diode laser 22 is sensitive not only to power levels but also to the phase of the feedback (reflected) light. Hence, in the absence of optical feedback stabilization, the length of any external cavity (e.g. the cavity defined by back mirror 25 and cavity input 32) coupled to diode laser 22 is a critical parameter affecting laser performance; stable operation of the diode laser would require extreme mechanical stability (<1Å excursions) for all external cavities.

A laser stabilization means 40 is situated in an optical path between laser output 24 and cavity input 30. Stabilization means 40 comprises a frequency shifting means for frequency-shifting light passing between laser output 24 and cavity input 30. The frequency-shifting means provides light shifted by an amount $\Delta v$, incident on laser output 24. The frequency shift (typically 50 to 500 MHz) introduced by the frequency-shifting means is preferably taken into account for high-resolution spectroscopy applications; a wavelength calibration of system 20 may then be performed. For short (<5 ns), non-Fourier-transform-limited pulses with wide linewidths (>1 GHz) and significant frequency jitter, typical frequency shifts may be neglected.

Preferably, the frequency-shifting means comprises an acoustooptic modulator (AOM) 44, which generates a frequency-shifted first-order beam 47 incident on cavity input 32 and a non-frequency-shifted zeroth order (diagnostic) beam 48 incident on optical diagnostic elements 70. AOM 44 shifts by $\Delta v/2$ the frequency of light extending from laser output 24, as well as of light reflected by various optical components (including cavity input 30) and incident on laser output 24. Light passing twice through AOM 44 is frequency-shifted by $\Delta v$. For information on acousto-optic modulators see for example Yariv, *Quantum Electronics*, John Wiley & Sons, New York, 1989. Briefly, in an AOM a pressure transducer creates a sound wave that modulates the index of refraction in an active nonlinear crystal through the photoelastic effect. The sound wave produces a Bragg diffraction grating that disperses incoming light into multiple orders. The diffracted light is frequency-shifted by an amount equal to the acoustic wave frequency, as can be illustrated by conservation of energy or Doppler-shift arguments.

Alternatively, the frequency shifting means can comprise an electro-optic modulator; for information on electro-optic modulators see for example Demtröder, *Laser Spectroscopy*, Springer, Berlin, 1996. The switching function of AOM 44 is then performed by a solid state switch for turning on and off the beam incident on cavity 30. The frequency-shifting means could also include a vibrating micromachined micro-optic (mirror) for Doppler-shifting reflected light by the frequency of its vibration.

The frequency-shifted feedback generated by AOM 44 forces diode laser 22 to cycle through all values of phase with a period equal to $1/\Delta v$. The behavior of diode lasers in the presence of frequency-shifted optical feedback is described by the Lang and Kobayashi equations (Lang and Kobayashi, IEEE J. Quant. Electron. QE-16:347 (1980)). For a detailed treatment of diode laser stabilization using frequency-shifted optical feedback see the article by Martin et al. in *Optics Communications* 112:109–121 (1994), herein incorporated by reference. The phase-cycling stabilizes the time-averaged behavior of diode laser 22, narrowing its linewidth and eliminating the necessity of maintaining extremely stable external cavity lengths.

In order to achieve adequate stabilization and fast-enough switch-off times, the period of the frequency shift $\Delta v$ should not exceed the ring-down rates to be measured. Preferably, $1/\Delta v$ is less than the ring-down rate to be measured by at least an order of magnitude (a factor of ten). Typically, a frequency shift $\Delta v$ greater than several MHz is sufficient for good quality ring-down reflectors (R>99.99%, corresponding to ring-down times on the order of tens of $\mu s$), and will eliminate any changes in phase shift associated with changes in length of the external cavity. Under these conditions, the effective linewidth of diode laser 22 becomes insensitive to both thermal (seconds time scale) and mechanical (milliseconds time scale) perturbations in external cavity length(s).

Selecting a frequency-shifted feedback intensity suitable for adequate stabilization of diode laser 22 is critical in the present invention. Diode laser 22 is stabilized only by feedback levels within a certain range, which may be system dependent. The selection of an appropriate level may be optimized according to the system and application of interest, as is apparent to the skilled artisan. For information on selecting appropriate frequency-shifted feedback levels see the above-referenced book by Coldren and Corzine, *Diode Lasers and Photonic Integrated Circuits*. Typically, low frequency-shifted feedback levels (less than −65 dB) may be insufficient for adequate stabilization, while high frequency-shifted feedback levels (larger than −35 dB) may cause instability in diode laser 22. Suitable feedback levels are commonly between −35 dB and −65 dB (equivalently, 35 dB to 65 dB isolation). The feedback level used for stabilizing diode laser 22 is preferably between −45 dB and −55 dB. The feedback level is measured in decibels as 20 times the logarithm (base 10) of the ratio of frequency-shifted feedback intensity to laser output intensity. Preferred feedback levels correspond approximately to intensity ratios between 1/100 and 1/1000.

FIG. 2-A illustrates the improvement in linewidth in a feedback-stabilized system of the present invention, relative to a conventional system lacking stabilization. The linewidth for a prior-art free-running diode laser (dashed line) is much broader than for a diode laser stabilized with frequency-shifted feedback (−36 dB) from a resonant cavity (solid line)

In the presence of feedback stabilization, the narrowest achievable linewidth for each feedback level depends on the external cavity length, (see the above-incorporated article by Martin et al. (1994)). FIG. 2-B illustrates diode laser linewidths as a function of external cavity length, in the presence of first order feedback (50 dB) only, for three cavity lengths: $L_{ext}$=215 cm (solid line), $L_{ext}$=100 cm (dashed line), and $L_{ext}$=55 cm (dash-dotted line). Longer external cavities generally allow narrower linewidths, as the free spectral range (FSR) of a cavity is inversely proportional to its total roundtrip length.

The distribution of light between orders can be varied by controlling the orientation of the incoming light relative to the sound wave (Bragg angle) and the crystal axes of AOM 44. The driving power of AOM 44 determines the diffraction efficiency and hence the amount of feedback to diode laser 22. For particular orientations, most incoming light (60–80%) can be directed into a desired order, for example the first order. Thus, AOM 44 serves as a feedback control element for controlling the intensity of reflected light (feedback) incident on diode laser 22. Additional feedback control is achieved using a Faraday optical isolator 46, which reduces the amount of reflected light reaching laser output 24. Preferably, isolator 46 is situated in the optical path between laser output 24 and AOM 44, such that isolator 46 isolates laser 22 from direct reflections from AOM 44. The level of frequency-shifted feedback incident on diode laser 22 is determined primarily by the losses introduced by isolator 46 and AOM 44.

The first order diffraction feedback provided by the reflection of beam 47 from cavity input 32 drives the phase of diode laser 22 and stabilizes its linewidth. Preferably, no zeroth order feedback is provided to laser 22. If desired, the linewidth of diode laser 22 may be broadened by non-frequency-shifted feedback provided by the reflection of beam 48 from suitable optical components. If linewidth broadening is desired, zeroth order (non-frequency-shifted) feedback should be within an order of magnitude (factor of 10) of the first order (frequency-shifted) feedback. The zeroth order feedback allows multiple external cavity modes to exist. The first order feedback cyclically chirps the output of diode laser 22 through these modes at twice the driver frequency of AOM 44 ($\Delta v$). If zeroth order feedback is not desired, beam 48 may be dumped such that no reflection of beam 48 are incident on laser 22. FIG. 2-C shows linewidths for a laser under frequency-shifted feedback (−50 dB) only, and under frequency-shifted (−50 dB) and non-frequency-shifted feedback (−50 dB).

Controlling the relative intensities of zeroth and first order feedback allows modulating the linewidth of diode laser 22. The linewidth of light emitted by diode laser 22 is preferably broad enough that at least one longitudinal mode and its associated transverse modes are excited in cavity 30. Increasing the relative intensity of non-frequency-shifted feedback increases the number of excited external cavity modes, and thus the linewidth of diode laser 22. The resulting flexibility in achievable linewidth in turn facilitates various CRDS applications.

The linewidth of diode laser 22 may vary with the wavelength of light emitted, as illustrated in the Example below and in FIGS. 3-A and 3-B. Suboptimal packaging may lead to non-uniform heating of diode laser 22, and consequently to strain on laser output 24. Such strain may change the reflectivity of laser output 24, and thus the coupling of feedback light into diode laser 22. Other factors which may affect the phase of diode laser 22 and hence its linewidth include changes in carrier density noise, or in index of refraction or carrier confinement within diode laser 22. Such factors were observed to be fairly negligible for small (<10° C.) changes in the temperature of diode laser 22, and thus not directly responsible for substantial linewidth variations.

Variations in linewidth with wavelength increase baseline noise, and are therefore undesirable. Such variations are preferably minimized, in particular by adjusting the relative magnitudes of frequency-shifted and non-frequency-shifted feedback so as to maintain the laser linewidth constant throughout a wide spectrum of wavelengths. For measurements over a narrow spectrum of wavelengths, such as measurements over one or two lines of a given species, feedback adjustments with wavelength are generally not required. The linewidth of diode laser 22 was observed to remain relatively constant for small temperature excursions (ca. 2° C.) and correspondingly small wavelength excursions (ca. 0.1 nm) (see FIG. 3-A).

AOM 44 also serves as a high-speed, mechanically stable switch. Function generator 84 is connected to AOM 44, and drives AOM 44 with square waves or step-functions. Function generator 84 drives AOM 44 to rapidly deflect light into and out of its first order, by switching on and off the RF power driving the pressure transducer of AOM 44. When the RF power is on, the first order throughput (the intensity of beam 47) is maximized; when the RF power is off, the first order throughput is zero. AOM 44 is capable of achieving rise/fall times under 10 ns. For information on the use of AOMs as optical switches see for example the above-referenced books by Demtröder, *Laser Spectroscopy*, and Siegmann, *Lasers*, and the above-incorporated article by Martin et al. (1994).

The following example is intended to illustrate the invention, and should not be construed to limit the invention.

EXAMPLE

A system of the present invention was used to characterize laser performance and obtain spectral data for water vapor at 1 atm and 5 Torr. The diode laser employed was a Sharp LT017MD single-mode (V-channel current blocking) GaAlAs DL, with mirror reflectivities of about 90% for the back mirror and 5% for the laser output. The threshold current of the DL was typically 60 mA when free-running. The DL was operated with both current and temperature stabilization (Peltier heater/cooler) provided by a laser diode controller (Melles Griot:06DDL203 and 06DTC007). The free-running diode produced about 40 mW output power at 812 nm for 26° C. and 100 mA operating current $I_{op}$. Wavelength scans were performed by current-tuning the diode for small wavelength excursions (0.001 nm=0.015 cm$^{-1}$ at 810 nm with a 0.01 nm/mA rate) and temperature-tuning for larger wavelength excursions (0.1 nm=0.15 cm$^{-1}$ at 810 nm with a 0.05 nm/°C. rate). The DL output remained stable over 1.2 nm (812.6–813.8 nm), but only 0.6 nm (813.2–813.8 nm) were used for the spectroscopy of water vapor. The bandwidth of the free-running device was independently measured to be about 50 MHz.

DL linewidth control was performed with feedback from both first and zeroth orders. For broad linewidth measurements, first order feedback was varied between −48 dB and 52 dB, while zeroth order feedback was varied between −47.6 dB and −51.7 dB. The −48 dB level is closer to the instability regime than the −52 dB level. The isolator situated between the DL and the AOM provided 36–40 dB isolation. The feedback levels were estimated with the help of a beamsplitter (not shown in FIG. 1) placed immediately at the DL output.

The system was mounted on a vibration-isolated movable optical table (Newport:VW Series Workstation), but otherwise no special precautions were taken against thermal motion of the optical elements, even of the ring-down resonator. The output of the laser was collimated with a NA=0.25 lens, and passed through a pinhole and then an optical isolator (OFR:IO-5-NIR-LP) before reaching the AOM (Brimrose:GPM-400-100-960 with FFA-400-B2-F1 driver). The laser was focused to a spot size of about 60 μm at the center of the AOM crystal, and was recollimated after the AOM. The RF driver of AOM was modulated with a square wave output from a function generator (HP:8116A).

Diagnostic components included a fiber-coupled wavelength meter with 0.001 nm resolution (Advantest:TQ8325), and a scanning confocal interferometer (Burleigh:8 GHz SA$^{Plus}$ Analyzer with RG-91 driver, DA-100 detector). The beamsplitter in the diagnostics achieves a 65/35 split with 65% of the light reaching the wavelength meter.

The ring-down cavity was 45.7 cm in length, comprised two 1" mirrors with 1 m radius and 99.97% reflectivity (Newport:10CV00.SR.40F), and was enclosed in a vacuum chamber with 2" sapphire windows. Cavity adjustment was made via flexible bellows fixed in gimbal mounts (MDC:FGC-275-M). Such a stable rather than confocal optical cavity configuration was chosen to provide a fairly dense mode structure that was found to increase output signal levels and reduce shot-to-shot fluctuations in cavity coupling and hence time constant.

Cavity pressures were measured with both a baratron (MKS:PDR-D1) and a convection gauge (Granville-Phillips:Model 275). Before any sample was introduced for measurement, the cavity was purged below 1 mTorr using a mechanical pump with a liquid nitrogen trap. All background scans were also taken at this pressure. For low pressure measurements, a constant water vapor pressure was established in the cavity by adjusting both the cavity evacuation rate and the water vapor inflow rate. Stable flows ranging from 20 mTorr to 10 Torr in cavity pressure were thus established. When measuring water vapor in room air, the pump was removed, and the valve opened to let air into the cavity.

Detection at the cavity output was performed with a photomultiplier tube (Hamamatsu:R2658P with SRS PS 325 high-voltage supply) and a photon-counting scalar (SRS:SR430). The cavity output was attenuated with an ND=2 filter in order to prevent overflow of the scalar's counting bins. Later, the attenuator was removed, and the output signal of the photomultiplier was directly digitized on an oscilloscope (HP:54510A).

FIG. 3-A illustrates the dependence of linewidth with wavelength/temperature for wavelengths between 813.2 nm and 813.8 nm. FIG. 3-B shows the spectral output at 813.2 nm (dashed line) and 813.6 nm (solid line). The figures represent data taken in the presence of both first and zeroth order feedback (−50 dB each). Total FWHM linewidths ranging from 500 MHz at lower tuning temperatures/wavelengths (30° C./813.2 nm) to 240 MHz at higher tuning temperatures/wavelengths (40° C./813.6 nm) were observed, and are shown in FIG. 3-A. At these laser linewidths, at least one longitudinal mode, and its associated transverse modes were always excited in the ring-down resonator; similar observations were made for low pressures scans made with narrower linewidths (180 to 240 MHz). The decrease in linewidth illustrated in FIG. 3-A and the associated decrease in the number of excited external cavity modes indicate that the overall DL dynamics depend on temperature.

The ring-down decay obtained from either the scalar or the oscilloscope was fitted on a personal computer using the Levenberg-Marquardt algorithm with the initial guess being provided by a linear least squares fit of the logarithm of the signal. This scheme, first proposed by Naus et al. (*ILS-XII 12th Interdisciplinary Laser Science Conference*, ed. A. P. Society, OSA, Rochester, N.Y., 1996, p. 122) correctly fits exponential decays with a constant offset, as is typical for a photomultiplier output. Taking into account constant offsets becomes especially important when a large dynamic range in ringdown constant is desired, for example when both very weak and very strong lines are simultaneously present in a spectrum or when large fluctuations in concentration for a given species are being measured.

FIG. 4-A shows ring-down waveforms as recorded using an oscilloscope, while FIG. 4-B shows a ring-down waveform as recorded using a multichannel scalar. Each data point in FIG. 4-A contains the average of 300 shots, while each data point in FIG. 4-B contains the average of 5000 shots, according to the present invention. FIGS. 4-A and 4-B show actual averaged signals that were fitted to obtain ring-down decay rates. Over a millisecond time interval, the stabilized DL is coupled into the unstabilized resonator every time that the AOM diffracts light into the first order, because the linewidth exceeds the cavity free spectral range. Effectively, the AOM modulation square wave at 10 kHz is convolved with the cavity response, producing an exponential signal build up ('ring-up') and an exponential decay ('ring-down') with equal time constants. For sufficiently fast sampling electronics, both ring-down and ring-up time constants can be measured, and time constant acquisition rates on the order of kHz (depending on the quality of the cavity mirrors) can be achieved. Ring-down measurements are preferred in a method of the present invention, since measurements of ring-up time constants are generally more susceptible to laser noise than measurements of ring-down time constants.

On closer inspection of the coupling, it was found that there was a variation (about 5%) in the intensity of the light coupled into the sample cavity. This RMS variation corresponds to different numbers of modes being excited within the sample cavity. This cavity mode number variation is a source of baseline noise. In the implementation described above, the sample cavity mode number variation led to noise of about 1% from shot to shot at a fixed wavelength in an evacuated environment, and about 4% from shot to shot in room air. By averaging over 300 shots on the oscilloscope and 5000 to 10,000 shots on the scalar, this variation was significantly reduced. Signal levels for both scalar and scope detection remained high, so that actual noise in the waveform itself remained below 1%, allowing accurate numerical fitting of the waveforms shown in FIGS. 4-A and 4-B.

FIGS. 5-A and 5-B show spectra of water vapor at 5 Torr and in room air, respectively. Each spectrum was obtained in one continuous scan. The detection limit was $2 \times 10^{-8}$ cm$^{-1}$ for 99.985% reflectors. The detection limit was calculated as the RMS baseline noise in an evacuated cell, divided by the quantity L/(1−R), where L is the path length and R is the mirror reflectivity. The detection limit was comparable to that of most pulsed CRDS systems, and was determined by the quality of our mirrors.

The spectrum in FIG. 5-B was obtained using maximum zeroth order feedback (−47.6 dB) to achieve the largest possible linewidth (240–500 MHz) and cavity coupling. Spectra at low pressures (<100 Torr) used less zeroth order coupling (−58 dB) to achieve a narrower laser linewidth (180–240 MHz) and to avoid convolution of the laser line with the absorbtion line. For more information on suitable relationships between linewidths and features of interest see the article by Hodges et al. in *Appl. Optics* 35:4112 (1996).

Scan step size in both cases remained limited to 0.001 nm resolution by the current step resolution (0.1 mA) of the DL driver. No baseline adjustments were made, but the overall baseline noise exceeds that reported by Romanini et al. (1997), and results from the excitation of multiple transverse modes in the cavity, which were used to improve light throughput.

The spectra shown in FIGS. 5-A and 5-B compare very favorably, in absolute frequency, linestrength and linewidth, to those generated by the HITRAN96 database (Rothman et al., *J. Quantitative Spectroscopy and Radiative Transfer* 48:469 (1992)). HITRAN is an acronym for HIgh Resolution Transmission molecular AbsorptioN database (http://www.hitran.com). The peak located at 813.224 nm, which appears in the spectra in FIGS. 5-A and 5-B, is not listed in HITRAN96, but can be found in table III of the article by Toth in *J. Molec. Spectroscopy* 166:176 (1994), where it is unassigned. The lines in FIGS. 5-A and 5-B belong to rotational transitions within the $2v_1+v_2+v_3$, $3v_1+v_2$, and $v_1+v_2+2v_3$ vibrational bands. The weakest peaks recorded in HITRAN96 were measurable with the system. These peaks, located at 813.452 nm (p2 in FIGS. 5-A and 5-B) and 813.391 nm (p1 in FIGS. 5-A and 5-B) correspond respectively to linestrengths of $6.33 \times 10^{-26}$ cm$^{-1}$/(molecule/cm$^2$) and $3.40 \times 10^{-26}$ cm$^{-1}$/(molecule/cm$^2$).

The nominal sensitivity to water vapor was 20 ppm in low pressure flows, and 200 ppm at 1 atm pressure. For the 'open air' CRDS measurements, the baseline, noise, and overall sensitivity were significantly degraded from those of the evacuated cell (the time constant decreased from 10 $\mu$s to 6 $\mu$s). This degradation is most likely caused by the deposition of dust and other airborne particles or droplets existing in the environment, because it was reproducibly eliminated by evacuating the ring-down cell. Such contamination of the high reflectors that are fundamental to CRDS sensitivity may limit the ultimate sensitivity of trace species detection systems for the ambient environment.

The nominal sensitivity of this system to water vapor (20 ppm at low pressure, 200 ppm at 1 atm) can be improved by not only choosing a stronger absorption band of water at 1.3647 $\mu$m, but also by designing fast analog detection electronics, averaging over more waveforms, obtaining better reflectors, and adding some cavity tracking or feedback to allow mode matching and controlled mode coupling. The sensitivity enhancement factor of each of these improvements is estimated at 1000, 5, 3, 10, and 10, respectively, leading to detection levels of sub ppb of water vapor under atmospheric conditions (and tens of ppt for low-pressure conditions).

All publications cited above are herein incorporated by reference in their entirety for all purposes to the same extent as if each individual publication was specifically and individually indicated to be so incorporated by reference.

It will be clear to one skilled in the art that the above embodiments may be altered in many ways without departing from the scope of the invention. For example, ring-up or phase-shift CRDS may be used in the present invention, as is apparent to the skilled artisan. Moreover, the present invention is not limited to CRDS applications. Accordingly, the scope of the invention should be determined by the following claims and their legal equivalents.

what is claimed is:

1. A spectroscopy system with active optical feedback stabilization, comprising:
    a) a diode laser having a laser output;
    b) a resonant cavity comprising a cavity input and a cavity output, defining an intracavity light path passing through a sample, and situated such that light extending from said laser output is incident on said cavity input;
    c) a laser stabilization means in optical communication with said laser output, for providing frequency-shifted feedback light incident on said laser output of a level suitable for stabilizing said laser; and
    d) a detector in optical communication with said cavity output, for detecting light extending from said cavity output, thereby measuring an interaction of said sample with intracavity light.

2. The system of claim 1 wherein said laser stabilization means comprises an acousto-optic modulator for generating said frequency-shifted feedback light by frequency-shifting light generated by said laser.

3. The system of claim 2 further comprising a driving means for driving said acousto-optic modulator and for controlling a strength of a diffraction grating formed by said acousto-optic modulator, thus controlling an intensity of said frequency-shifted feedback light.

4. The system of claim 3 wherein said laser stabilization means further comprises an optical isolator for controlling said intensity of said frequency-shifted feedback light.

5. The system of claim 4 wherein said isolator is situated in an optical path between said laser output and said acousto-optic modulator, whereby said isolator isolates said laser from direct reflections from said acousto-optic modulator.

6. The system of claim 1 wherein said level is between 35 dB and 65 dB.

7. The system of claim 1 wherein said level is between 45 dB and 55 dB.

8. The system of claim 1 wherein said laser is an infrared laser.

9. The system of claim 1 wherein said laser is tunable.

10. The system of claim 1 further comprising a data analysis means in communication with said detector, for receiving a signal characterizing said interaction, and determining from said signal a value of a parameter of interest characterizing a time-dependence of an intensity of said intracavity light.

11. The system of claim 10 wherein said parameter of interest is an exponential rate characterizing said time-dependence.

12. The system of claim 10 wherein said parameter of interest is a ring-down rate.

13. The system of claim 1 wherein said laser is a continuous wave laser, and said system further comprises a switching means in optical communication with said laser output, for switching on and off said light incident on said cavity input.

14. The system of claim 13 wherein said switching means comprises an acousto-optic modulator.

15. The system of claim 1 wherein said laser output has a reflectivity of less than 20%.

16. An optical system with active feedback stabilization and linewidth control, comprising:
    a) a diode laser having a laser output;
    b) a resonant cavity comprising a cavity input and a cavity output, defining an intracavity light path passing through a sample, and situated such that light extending from said laser output is incident on said cavity input;
    c) a laser stabilization means in optical communication with said laser output, for providing frequency-shifted feedback light incident on said laser output for actively stabilizing said laser;
    d) a linewidth broadening means in optical communication with said laser output, for providing nonfrequency-shifted feedback light incident on said laser output, for increasing a linewidth of said laser; and e) a detector in optical communication with said cavity output, for detecting light extending from said cavity output, thereby measuring an interaction of said sample with intracavity light.

17. An optical system comprising:

a) a diode laser having a laser output and a back mirror;

b) a resonant cavity comprising a cavity input and a cavity output, defining an intracavity light path passing through a sample, and situated such that light extending from said laser output is incident on said cavity input;

c) a laser stabilization means situated in an external cavity defined between said back mirror and said cavity input, for frequency-shifting light generated by said laser and reflected by said cavity input for providing frequency-shifted feedback light incident on said laser output such that said feedback light stabilizes said laser; and d) a detector in optical communication with said cavity output for detecting light extending from said cavity output, for measuring an absorption spectrum of said sample.

18. An optical system comprising:

a) a resonant cavity for holding a sample, having a cavity input and a cavity output;

b) a continuous wave, tunable diode laser having a laser output in optical communication with said cavity input, for generating light incident on said cavity input, thus generating intracavity light comprising a wavelength corresponding to an absorption region of interest of said sample, wherein a time-dependence of an intensity of said intracavity light of said wavelength is determined by an absorption of said sample at said wavelength;

c) an acousto-optic modulator situated in an optical path between said laser output and said cavity input, for frequency-shifting light emitted by said laser and light reflected from said cavity input, thus providing frequency-shifted feedback light incident on said laser output such that said frequency-shifted feedback light stabilizes said laser;

d) a detector in optical communication with said cavity output, for detecting said time-dependence; and e) a data analysis means in electrical communication with said detector, for generating an absorption spectrum of said sample from data on said time-dependence for a plurality of wavelengths.

19. The system of claim 18 further comprising an optical isolator situated in an optical path between said laser output and said acousto-optic modulator, for controlling an intensity of said frequency-shifted feedback light incident on said laser output.

20. A method of performing an optical measurement, comprising the steps of:

a) using a diode laser to generate light comprising a wavelength corresponding to an absorption region of interest of a sample;

b) illuminating said sample with said light, wherein said sample is situated within a resonant cavity;

c) providing frequency-shifted feedback light to said laser by frequency-shifting light reflected from said resonant cavity and incident on said diode laser, for stabilizing said laser; and d) measuring a time-dependence of an intensity of intracavity light of said wavelength.

21. The method of claim 20 wherein said step of providing frequency-shifted feedback light to said laser comprises using an acousto-optic modulator to frequency-shift said light reflected from said resonant cavity.

22. The method of claim 20 further comprising providing non-frequency-shifted feedback light to said laser, for broadening a linewidth of said laser.

23. A method of controlling a diode laser linewidth in a feedback-stabilized spectrometer, comprising the steps of:

a) using a diode laser to generate light comprising a wavelength corresponding to an absorption region of interest of a sample;

b) illuminating said sample with said light, wherein said sample is situated within a resonant cavity;

c) providing frequency-shifted feedback light to said laser by frequency-shifting light reflected from said resonant cavity and incident on said diode laser, for stabilizing said laser;

d) providing non-frequency-shifted feedback light to said laser, for broadening a said diode laser linewidth;

e) adjusting said frequency-shifted feedback light and said non-frequency-shifted feedback light such that said diode laser linewidth has a predetermined value; and f) measuring a time-dependence of an intensity of intracavity light of said wavelength.

* * * * *

UNITED STATES PATENT AND TRADEMARK OFFICE
CERTIFICATE OF CORRECTION

Page 1 of 1

| | |
|---|---|
| PATENT NO. | : 5,903,358 |
| APPLICATION NO. | : 08/949241 |
| DATED | : May 11, 1999 |
| INVENTOR(S) | : Zare et al. |

It is certified that error appears in the above-identified patent and that said Letters Patent is hereby corrected as shown below:

In The Specification Under Column 1:

• Please replace Column 1, line no. 11-16 with:

-- FEDERALLY-SPONSORED RESEARCH OR DEVELOPMENT
This invention was made with Government support under contract DE-FG03-92ER14304 awarded by the Department of Energy. The Government has certain rights in this invention. --

Signed and Sealed this
Thirteenth Day of March, 2012

David J. Kappos
*Director of the United States Patent and Trademark Office*